(12) United States Patent
Zhang et al.

(10) Patent No.: US 9,399,611 B2
(45) Date of Patent: Jul. 26, 2016

(54) METHOD OF ACETALIZING AN ALDEHYDE (71) Applicant: Agency for Science, Technology and Research, Singapore (SG)

(72) Inventors: Yugen Zhang, Singapore (SG); Jackie Y. Ying, Singapore (SG); Mei Xuan Tan, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/385,122

(22) PCT Filed: Mar. 15, 2013

(86) PCT No.: PCT/SG2013/000107
§ 371 (c)(1),
(2) Date: Sep. 12, 2014

(87) PCT Pub. No.: WO2013/137830
PCT Pub. Date: Sep. 19, 2013

(65) Prior Publication Data
US 2015/0080612 A1 Mar. 19, 2015

(30) Foreign Application Priority Data
Mar. 15, 2012 (SG) .............................. 201201905-5

(51) Int. Cl.
*C07C 41/16* (2006.01)
*B01J 31/02* (2006.01)
*C07B 41/04* (2006.01)

(52) U.S. Cl.
CPC ............. *C07C 41/16* (2013.01); *B01J 31/0244* (2013.01); *C07B 41/04* (2013.01)

(58) Field of Classification Search
None
See application file for complete search history.

(56) References Cited

U.S. PATENT DOCUMENTS

| | | | |
|---|---|---|---|
| 4,487,972 A * | 12/1984 | Haag | ........................ B01J 31/08 208/16 |
| 2013/0189175 A1* | 7/2013 | Zhang | .................... B01D 53/02 423/228 |

FOREIGN PATENT DOCUMENTS

| | | |
|---|---|---|
| WO | WO-2012/039683 | 3/2012 |
| WO | WO-2013/137830 | 9/2013 |

OTHER PUBLICATIONS

"Compound (2,2',2"-(2,6,8,10,12,16,18,20,22,26,28,30,31,32,33-pentadecaazatetracyclo[25.3.1.17,11.117,21 ]tritriaconta-1(31),7,9,11(33),17,19,21(32),27,29-nonaene-9, 19,29-triyltriimino)tris-ethanol", CAS RN 508168-15-8, STN Entry Date May 1, 2003.

"International Application No. PCT/SG2013/000107, International Preliminary Report on Patentability mailed Jul. 8, 2014", 20 pgs.

"International Application No. PCT/SG2013/000107, International Search Report mailed Jul. 26, 2013", (Jul. 26, 2013), 6 pgs.

Fan, Da-He, et al., "An efficient and chemoselective procedure for acylal synthesis", Molecules, 15(9), (Sep. 16, 2010), 6493-501.

Li, Nai-Hong, et al., "Reagents and catalysts derived from polybenzimidazole and polystyrene resins with imidazole pendant groups", Reactive Polymers, Ion Exchangers, Sorbents, 6(2-3), (Oct. 1987), 311-321.

Wang, Wei, et al., "Self-assembly synthesis of a high-content sulfonic acid group functionalized ordered mesoporous polymer-based solid as a stable and highly active acid catalyst", J. Mater. Chem., 2012, 22(31), 15874-15886, (Jun. 7, 2012), 15874-15886.

Yamada, Yudai, et al., "Preparation and catalytic use of silica-polymer core-shell microspheres with imidazolium-styrene copolymer shells", Catalysis Communications, 11(4), (Dec. 15, 2009), 227-231.

Yang, S. J, et al., "Catalytic synthesis of acetals and ketals with $H_3PW_{12}O_{40}PAn$", Rare Metals, 27(1), (Feb. 2008), 89-94.

"European Application No. 13761017, Supplementary European Search Report dated Aug. 11, 2015", 4 pgs.

Perles, Josefina, et al., "First high thermally stable organo-inorganic 3D polymer scandium derivative as a heterogeneous Lewis acid catalyst", Chem. Commun., 2003, 346-347, (Jan. 3, 2003), 346-347.

Rezaei, Ramin, et al., "Microwave Assisted, Solvent Free One Pot Synthesis of Nitriles Aryl Aldehydes on Melamin Formaldehyde as Solid Support", Chin. J. Chem. 2010, 28, 993-996, (Mar. 16, 2010), 993-996.

* cited by examiner

Primary Examiner — Rosalynd Keys
(74) Attorney, Agent, or Firm — Schwegman Lundberg & Woessner, P.A.

(57) ABSTRACT

A method of acetalizing an aldehyde comprising reacting said aldehyde with an alcohol in the presence of a polymeric catalyst to form an acetal wherein the polymeric catalyst is a mesoporous poly-melamine-formaldehyde polymer.

12 Claims, 1 Drawing Sheet

METHOD OF ACETALIZING AN ALDEHYDE

PRIORITY CLAIM TO RELATED APPLICATIONS

This application is a U.S. national stage application filed under 35 U.S.C. §371 from International Application Serial No. PCT/SG2013/000107, which was filed Mar. 15, 2013, and published as WO 2013/137830 on Sep. 19, 2013, and which claims priority to Singapore Application No. 201201905-5, filed Mar. 15, 2012, which applications and publication are incorporated by reference as if reproduced herein and made a part hereof in their entirety, and the benefit of priority of each of which is claimed herein.

TECHNICAL FIELD

The present invention generally relates to a method of acetalizing an aldehyde. The present invention also relates to a catalyst for acetalizing an aldehyde.

BACKGROUND

The protection of carbonyl compounds, in particular aldehydes, by acetalization is a common and useful technique for multi-step synthesis in drug design, organic and carbohydrate chemistry, and in the pharmaceutical industry. Acetals are also commonly used in detergents, cosmetics and fragrances. Acetalization serves to protect the carbonyl group from the attacks of several reagents such as nucleophiles, oxidants, hydrides and organo-metallic reagents.

A typical method of acetalization involves a reaction with alcohol or diol using an inorganic acid such as hydrochloric acid as the catalyst. In this reaction, water is usually removed from the reaction to shift the equilibrium towards the right to increase product yield. The removal of water may be achieved by physical processes such as azeotropic distillation, or through chemical means such as the addition of drying agents to the reaction e.g., trialkylorthoformate. However, the use of corrosive hydrochloric acid (HCl) remains a disadvantage.

Many other types of catalysts have also been reported to catalyze the acetal protection of carbonyls. These catalysts include conventional acids such as trifluoroacetic acid (TFA), p-Toluenesulfonic acid (p-TSA), Lewis acids; functionalized silica; metal chlorides; metal triflates; transition metal complexes; natural materials such as kaolinitic clay; and organic compounds such as N-bromosuccinimide (NBS), 2,6-pyridinedicarboxylic acid (PDA), trichloromethylsilane and tetrabutylammonium tribromide (TBATB). Acetalization carried out under basic conditions, involving the use of $NH_3$ and $Et_3N$ with $TiCl_4$ catalyst are also known.

However, the above-mentioned conventional means and list of catalysts do not overcome the disadvantages and limitations which comprises the use of corrosive acid catalyst, high reaction temperatures (such as greater than 60° C. to 150° C.), expensive reagents, poor chemo-selectivity, incompatibility for substrates containing acid-sensitive functional groups, and difficulty in catalyst recovery and recycling without loss in catalytic activities.

Accordingly, there is a need for a catalyst that ameliorates the above limitations.

There is a need to provide a method of acetalizing an aldehyde that overcomes, or at least ameliorates, one or more of the disadvantages described above.

SUMMARY

According to a first aspect, there is provided method of acetalizing an aldehyde comprising reacting the aldehyde with an alcohol in the presence of a polymeric catalyst to form an acetal.

Advantageously, the method may not require the use of high reaction temperatures, such as for example, a reaction temperature above 100° C.

Advantageously, the method may be conducted neat without the use of any co-solvents. Advantageously, the method may be conducted without the use of any metals or metal catalysts.

Advantageously, the method may not require the use of additional pH-adjusting solvents or substrates. Hence, acid-sensitive substrates may be used in the method.

According to a second aspect, there is provided use of a polymeric catalyst to increase the rate of acetalization between an aldehyde and an alcohol.

Advantageously, the catalyst may have a high density of methylene diamine groups that can provide double hydrogen bonding to aldehyde substrates. In addition, the catalyst is slightly acidic. Accordingly, the presence of the methylene diamine groups and the weak acidity may confer dual functionalities to the catalyst as a heterogeneous catalyst for the acetalization of aldehydes.

Advantageously, the catalyst may be chemo-selective to aldehydes, with minimal or no reaction with ketones. Hence, the catalyst may be useful for the protection of aldehydes in the presence of ketones or acid-sensitive groups.

Advantageously, the catalyst may have a high surface area due to its porous nature.

Advantageously, the catalyst may be easily filtered and separated from a reaction mixture. As such, the catalyst may be easily reused without any substantial loss in catalytic activity.

Advantageously, the catalyst is a metal-free catalyst. Hence, the catalyst may not have any toxic effects that are commonly associated with a metal catalyst.

According to a third aspect, there is provided a polymeric catalyst comprising monomers that are capable of participating in double hydrogen bonding with an aldehyde, wherein said polymeric catalyst has a pH in the range of 4 to 6 and wherein said polymeric catalyst increases the rate of acetalization between the aldehyde and alcohol.

According to a fourth aspect, there is provided a method of making a polymeric catalyst comprising reacting melamine with formaldehyde in the presence of a non-aqueous polar solvent.

DEFINITIONS

The following words and terms used herein shall have the meaning indicated:

The term "catalyst" is to be interpreted broadly to refer to a material that is able to initiate a reaction or increase the rate of a reaction as compared to the rate of reaction that is conducted without the catalyst.

The term "surface area" as used in the context of the present specification is taken to refer to the surface area as determined by the Brunauer Emmett Teller (BET) method ("$S_{BET}$"), which is the standard measurement of particulate surface area by gas porosimetry techniques and as will be well known to persons skilled in the art. The gas used in the BET analysis is typically nitrogen.

The term "mesopore" and grammatical variations thereof, as used in the context of the present specification is taken to refer to pores residing within a polymeric catalyst having a pore diameter, as measured via the BJH method, of between 2 nm to 50 nm.

The term "micropore" and grammatical variations thereof as used in the context of the present specification is taken to refer to pores residing within a polymeric catalyst having a pore diameter, as measured via the BJH method, of 2 nm or less.

The term "nanoparticle" and grammatical variations thereof, as used in the context of the present specification, refers to a macromolecular structure formed from a plurality of repeating monomer units, in the nanometer range of less than 1 micron.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a method of acetalizing an aldehyde will now be disclosed.

The method comprises reacting an aldehyde with an alcohol in the presence of a polymeric catalyst to form an acetal.

The aldehyde may be any organic compound that has a formyl (—CHO) functional group. The type of aldehyde that can be acetalized by the catalyst is not limited and may include any aliphatic, branched, cyclic or aromatic aldehydes. Exemplary aldehydes that can be acetalized by the catalyst may be selected from the group consisting of cinnamaldehyde, benzaldehyde, alkoxybenzaldehyde (such as methoxybenzaldehyde), halobenzaldehyde (such as chlorobenzaldehyde or bromobenzaldehyde), methyl-formylbenzoate, biphenyl-4-carboxaldehyde, salicylaldehyde, trans-nitrocinnamaldehyde, methyl-trans-cinnamaldehyde and naphthaldehyde. In one embodiment, the aldehyde may not have an electron-withdrawing group in the para-position such as 4-nitrobenzaldehyde or 4-cyanobenzaldehyde).

The alcohol may be any organic compound that has a hydroxyl (—OH) functional group. The alcohol may have one hydroxyl functional group or may have two hydroxyl functional groups (that is, a diol). The alcohol may have one to six carbon atoms. Exemplary alcohols that may be used during acetalization of the aldehydes may be selected from the group consisting of methanol, ethanol, propanol, butanol, pentanol, hexanol, methanediol, ethanediol (such as 1,2-ethanediol), propanediol (such as 1,3-propanediol or 1,2-propanediol), butanediol (such as 1,4-butanediol, 1,3-butanediol, 1,2-butanediol or 2,3-butanediol), pentanediol (such as 1,5-pentanediol, 1,2-pentanediol, 2,3-pentanediol, 2,4-pentanediol 1,3-pentanediol, 1,4-pentanediol or 2-Methyl-2,4-pentanediol) and hexanediol (such as 1,6-hexanediol, 1,2-hexanediol, 1,3-hexanediol, 1,4-hexanediol, 1,4-cyclohexanediol, 1,5-hexanediol and 2,5-hexanediol).

The method may comprise adding a drying agent or a water scavenger to the reaction mixture in order to remove water, which is produced as a by-product of the acetalization reaction, to increase the yield of the acetal from the aldehyde. The drying agent may be a trialkyl orthoformate selected from the group consisting of trimethyl orthoformate, triethyl orthoformate, tripropyl orthoformate, and tributyl orthoformate. The amount of drying agent that can be added may be selected from the range of about 1 equivalent to about 2 equivalent, based on the amount of aldehyde.

The method may be carried out at a reaction temperature of about 25° C. to about 80° C. The reaction temperature may be room temperature (which is in the range of about 25° C. to about 30° C.), 40° C., 60° C. or 80° C.

The amount of the alcohol substrate to that of the aldehyde may be in a ratio in the range of about 5:1 to about 50:1 (where the amount of the alcohol is defined by its volumetric amount (in ml or l) and the amount of the aldehyde substrate is defined by its molar amount (in mmol or mol The amount of catalyst that can be used may be in the range of about 2 mg to about 50 mg of catalyst per 1 mmol of aldehyde. The amount of catalyst may be selected from the range of about 2 mg to about 10 mg, about 2 mg to about 20 mg, about 2 mg to about 30 mg, about 2 mg to about 40 mg, about 10 mg to about 50 mg, about 20 mg to about 50 mg, about 30 mg to about 50 mg and about 40 mg to about 50 mg. An increased catalyst amount may increase the yield of the acetalization reaction and/or reduce the reaction time required.

The reaction time may be dependent on the reaction temperature chosen and/or amount of catalyst used. A shorter reaction time can be obtained with a higher reaction temperature and/or a higher amount of catalyst used.

There is also provided use of a polymeric catalyst to increase the rate of acetalization between an aldehyde and an alcohol.

The polymeric catalyst may comprise monomers that are capable of participating in double hydrogen bonding with the aldehyde. The polymeric catalyst may have a pH in the acidic range when dissolved in water. The pH of the polymeric catalyst may be in the range of about 4 to about 6.

The polymeric catalyst may be porous. The polymeric catalyst may comprise monomers of melamine and formaldehyde. The polymeric catalyst may be poly-melamine-formaldehyde. The polymeric catalyst may be a mesoporous poly-melamine-formaldehyde (mPMF).

The polymeric catalyst may be composed of repeating units of a monomer having a ring structure (hereafter "ring monomer"). Each ring monomer unit may comprise at least three (such as 3 or 4 or 5 or 6) melamine monomer units, each melamine monomer unit being linked to the other two melamine monomer units by way of a linking group. The ring monomer may form a closed ring configuration having a substantially triangular orientation which may be further extended at each of the three terminal apexes.

A plurality of amine functional groups may extend around the periphery of each ring monomer. In particular, the amine groups may be disposed at the apexes of the ring monomer unit and adjacent to the linkages between one melamine monomer unit and another melamine monomer unit.

The amine functional group may be a secondary amine ($NHX_2$) or a tertiary amine ($NX_3$), where X may be selected from a melamine group, substituted or unsubstituted $C_{1-4}$ alkyl or alkenyl, or halogen. In one embodiment, the amine functional group is a secondary amine. Preferably, the secondary amine is NHYX, where X is a melamine group and Y is a linker between two amine functional groups, such as, a $C_{1-4}$ alkyl group. In another embodiment, Y can be a terminal alcohol group, such as a $C_{1-4}$ alcohol. In another embodiment, Y is a methanol group (—$CH_2OH$).

Advantageously, the ring monomer is regularly shaped and is capable of forming an extensive, tessellated, cross-linked lattice structure comprising repeating units of the ring monomers. During the formation of the catalyst, the interstitial spaces present between one ring monomer unit and its adjacent ring monomers promote the formation of the micropores within the catalyst structure, which are less than 2 nm in pore diameter. In one embodiment, the micropores may be less than 1 nm in pore size.

The cross-linked lattice structure comprising the melamine-formaldehyde co-polymer may form nanoparticles, which may aggregate to form a mesoporous network within the polymeric catalyst. In this regard, voids formed between adjacent clusters of these nanoparticles may form mesopores residing within the mesoporous polymeric catalyst.

The linking group may be an alkyl bridge extending between a pair of melamine groups, wherein the alkyl bridge comprises a lower alkyl group such as having 1 to 4, preferably 1 to 2 carbon atoms. It is preferred for the alkyl bridge to be a lower alkyl group to improve the rigidity of the ring monomer and to minimize steric hindrance caused by the linking group. In one embodiment, the alkyl bridge is methyl.

The poly-melamine-formaldehyde may have the basic structure as defined by Formula I below:

Formula I

As shown in Formula I, poly-melamine-formaldehyde has a high density of triazine rings and secondary amine groups linked by methylene groups. It is hypothesized that the high density of methylene diamine groups can provide double hydrogen bonding to the aldehyde substrate and hence catalyse the acetalization of the aldehyde, as shown by Schemes 1a and 1b which indicates the possible chemical bonding between the aldehyde and the catalyst.

Scheme 1b

Scheme 1a

Scheme 2 below shows the proposed mechanism for aldehyde activation over the polymeric catalyst via synergistic double hydrogen bonding.

Scheme 2

Here, the aldehyde initially gets absorbed onto the catalyst and the oxygen forms hydrogen bonding with the mPMF catalyst. This serves as a form of 'partial protonation' by means of hydrogen-bonding for the activation of aldehydes compound. Neighbouring alcohols which are bonded to mPMF via hydrogen bonding may be used as a co-reactant for acetalization. The neighbouring oxygen of the alcohol reacts via nucleophilic addition resulting in electrons migrating towards the carbonyl oxygen causing a large difference in electro-negativity between the two atoms. The electronegative carbonyl oxygen proceeds to form a third hydrogen bond and the carbonyl carbon carries a partial positive charge which makes it the primary target for another nucleophile (the oxygen of another alcohol in proximity). Therefore, the mPMF catalyst preferentially stabilizes the transition state via these synergistic hydrogen bondings. Eventually, after the second alcohol (oxygen) attacks the aldehyde in its transition state, water molecules and the actelized product formed dissociates from the mPMF catalyst.

The poly-melamine-formaldehyde may be slightly acidic. The inventors have found that when they stirred 1.8 g of poly-melamine-formaldehyde in 20 ml of deionized water, the pH of the poly-melamine-formaldehyde decreased to about 4.0.

Hence, the presence of the methylene diamine groups and the weak acidity of poly-melamine-formaldehyde confer dual functionalities to poly-melamine-formaldehyde as a heterogeneous catalyst for the acetalization reaction.

As such, there is provided a polymeric catalyst comprising monomers that are capable of participating in double hydrogen bonding with an aldehyde, wherein said polymeric catalyst has a pH in the range of 4 to 6 and wherein said polymeric catalyst increases the rate of acetalization between said aldehyde and an alcohol.

The polymeric catalyst may comprise mesopores disposed between melamine-formaldehyde co-polymer nano-particles and wherein micropores extend within the co-polymer nano-particles.

The total pore volume of the polymeric catalyst may include the total volume of the mesopores and the total volume of the micropores. The total pore volume of the polymeric catalyst may be in the range of about 0.6 $cm^3/g$ to about 3.5 $cm^3/g$, about 0.6 $cm^3/g$ to about 1.5 $cm^3/g$, about 1.0 $cm^3/g$ to about 3.5 $cm^3/g$ or about 1.14 $cm^3/g$ to about 3.46 $cm^3/g$.

The micropore volume may constitute about 2% to about 40%, about 5% to about 30%, about 6% to about 26%, or about 2% to about 7%, of the total pore volume. The micropore volume may be in the range from about 0.06 $cm^3/g$ to about 0.21 $cm^3/g$, about 0.09 $cm^3/g$ to about 0.17 $cm^3/g$, or about 0.06 $cm^3/g$ to about 0.14 $cm^3/g$.

Using the well-known Barrett-Joyner-Halenda (BJH) method, the pore sizes of the polymeric catalyst may be analyzed. The mesopores may have pore sizes in a range of about 5 nm to about 50 nm, from about 5 nm to about 45 nm, from about 5 nm to about 40 nm, from about 5 nm to about 35 nm, from about 5 nm to about 30 nm, from about 5 nm to about 25 nm, from about 5 nm to about 20 nm, from about 5 nm to about 15 nm, and from about 5 nm to about 10 nm. In one embodiment, the mesopores may have pore sizes in a range of about 5 nm to about 50 nm, or about 5 nm to about 20 nm. The pore sizes of the micropores may be about 2 nm or lesser; or about 1 nm or lesser.

The polymeric catalyst may possess a surface area of at least about 300 $m^2/g$ or at least about 600 $m^2/g$. The surface area of the polymeric catalyst may be in the range of about 600 $m^2/g$ to about 1200 $m^2/g$, about 400 $m^2/g$ or more, about 450 $m^2/g$ or more, about 500 $m^2/g$ or more, about 550 $m^2/g$ or more, about 600 $m^2/g$ or more, about 650 $m^2/g$ or more, about 700 $m^2/g$ or more, about 750 $m^2/g$ or more, about 800 $m^2/g$ or more, about 850 $m^2/g$ or more, about 900 $m^2/g$ or more, about 950 $m^2/g$ or more, about 1,000 $m^2/g$ or more, about 1050 $m^2/g$ or more, or about 1,100 $m^2/g$ or more. The surface area of the polymer catalyst may be about 930 $m^2/g$.

Due to the heterogeneous nature of the polymeric catalyst, the catalyst can be easily removed from the reaction mixture and reused. The catalyst can be removed from the reaction mixture by filtration or centrifugation. The catalyst may be reused for at least three times, at least four times, at least five times, at least, six times, or at least Seven times, without any substantial decrease in its catalytic activity.

The polymeric catalyst may be chemo-selective towards aldehydes so that the acetalization of the aldehydes can still be carried out even if ketones are present in the reaction mixture.

The poly-melamine-formaldehyde catalyst may be formed by reacting melamine with formaldehyde in the presence of a non-aqueous polar solvent.

The formaldehyde may be polymerized formaldehyde that has undergone condensation polymerization. The polymerized formaldehyde may comprise from about 8 to 100 carbon atoms. In one embodiment, the formaldehyde is paraformaldehyde.

The non-aqueous polar solvent may be an aprotic solvent, that is, a solvent that does not contain a dissociable proton ($H^+$ ion). The aprotic solvent may be a pH neutral solvent. Hence, it is not necessary to utilize any additional pH modifying steps when forming the poly-melamine-formaldehyde catalyst. The aprotic solvent may be selected from the general class of sulfones or sulfoxides. In one embodiment, the aprotic solvent is selected from an aliphatic sulfoxide, having a general formula of $R^1$—SO—$R^2$, wherein $R^1$ and $R^2$ may be same or different, and are independently selected from, substituted or unsubstituted $C_{1-9}$ alkyl and $C_{1-9}$ alkylene. In one embodiment, the aliphatic sulfoxide may comprise 2 to 10 carbon atoms. In another embodiment, the aliphatic sulfoxide may comprise 2 to 6 carbon atoms. In one embodiment, the aliphatic sulfoxide is dimethyl sulfoxide ($H_3C$—SO—$CH_3$).

Exemplary aprotic solvents may include, but are not limited to, dimethyl sulfoxide (DMSO), di-n-butyl sulfoxide, tetramethylene sulfoxide, methyl phenyl sulfoxide, and the like, as well as combinations of any two or more thereof. In one embodiment, the sulfoxide solvent is DMSO.

The polymeric catalyst may be formed using melamine and formaldehyde as the reactants, in the presence of DMSO, as shown by Scheme 3 below:

Scheme 3

The melamine reacts with the formaldehyde to form melamine-formaldehyde co-polymers which precipitate out of the reaction mixture as nano-particle flakes having a size in the region of 10 to 50 nm. The poor solubility of the melamine-formaldehyde co-polymers in the DMSO solvent induces precipitation. The flakes precipitate from the solvent as melamine-formaldehyde nano-particles comprising micropores within the structure of the nanoparticle flakes. As the nanoparticle flakes precipitate, they agglomerate with each other to form micro sized particles. This agglomeration connects the nanoparticle flakes, forming mesoporous within the network of connecting nanoparticles. Hence, the polymeric catalyst can be viewed as a particle having mesopores disposed between melamine-formaldehyde co-polymer nano-particles and wherein micropores extend within the co-polymer nano-particles.

The poly-melamine-formaldehyde catalyst may be formed at a temperature from about 120° C. to about 200° C., or from about 120° C. to about 170° C. The poly-melamine-formaldehyde catalyst may be formed at a temperature of about 140° C.

The non-aqueous polar solvent may be provided in admixture with an aqueous medium to form a co-solvent. In one embodiment, the aqueous medium is water. The non-aqueous polar solvent may be provided in admixture with water at a volume ratio selected from the range of 1:1 to 3:1, 1.5:1 to 3:1, 2:1 to 3:1, 2.5:1 to 3:1, 1:1 to 2.5:1, 1.5:1 to 2.5:1, 2:1 to 2.5:1, 1:1 to 2:1, 1.5:1 to 2:1, and 1:1 to 1.5:1. In one embodiment, the volume ratio of the polar solvent to water is 3:1. By adding water to the solvent mixture, the reaction temperature may be lowered to about 140° C.

The molar ratio of formaldehyde to melamine may be in a range from about 1 to about 5, from about 1.65 to about 4.5, from about 1.8 to about 3.75, from about 1.95 to about 3.0, from about 2.25 to about 3.0, from about 2.25 to about 3.75, or from about 1.5 to about 2.5.

The reaction may be undertaken for a period of from 48 hours to 120 hours. In one embodiment, the reaction step is performed for 72 hours.

Additional information on mPMF can be obtained from PCT application PCT/SG2011/000328, the disclosure of which is incorporated by reference.

The reaction step may be performed in a closed system, for example, a bomb reactor or a pressure reactor. In one embodiment, the reactants are placed inside a steel bomb reactor and exposed to high temperatures in a heater, such as an oven. In another embodiment, the reaction step may also be carried out in a partially heated reactor. In one embodiment, the reactants are introduced into a small volume glass vial and placed over a heated metal plate.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

DETAILED DESCRIPTION OF DRAWINGS

Figure 1A:
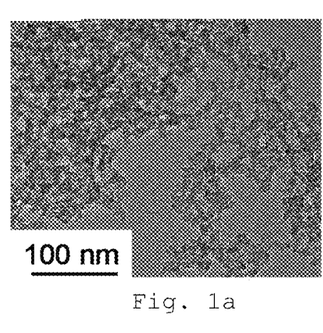
FIG. 1a is a transmission electron microscopy (TEM) image of the melamine-formaldehyde co-polymer intermediates during formation of the co-polymer. The scale bar in this image is 100 nm.

Referring to FIG. 1a, there is shown a TEM image of the melamine-formaldehyde co-polymer intermediates during formation of the co-polymer. Here, the nano-particle flakes in the region of 10-50 nm that are formed by precipitating melamine-formaldehyde co-polymers aggregate to form micro sized particles. This agglomeration connects the nano-particle flakes, forming mesopores within the network of connecting nano-particles.

Figure 1B:
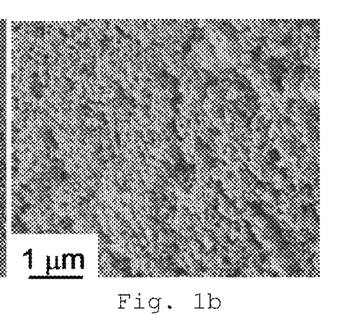
FIG. 1b is a scanning electron microscopy (SEM) image of the micron-sized synthesized melamine-formaldehyde co-polymer. The scale bar in this image is 1 microns.

Referring to FIG. 1b, there is shown the SEM image of the synthesized meso-porous melamine-formaldehyde co-polymer, having a particle size in the micron-size range.

EXAMPLES

Non-limiting examples of the invention and a comparative example will be further described in greater detail by reference to specific Examples, which should not be construed as in any way limiting the scope of the invention.

Generally, all chemicals and solvents were used as purchased (from Sigma-Aldrich of Missouri of the United States of America), unless otherwise stated. Gas chromatography-mass spectrometry (GC-MS) was performed with Shimadzu GC-2010 coupled with GCMS-QP2010. Nuclear magnetic resonance (NMR) spectra were obtained using a Brucker AV-400 (400 MHz) spectrometer. Nitrogen sorption analysis was performed on a Micromeritics Tristar 3000 at 77 K.

For the acetalization process, glassware was first dried in the oven at 100° C. before use. 2 mg of catalyst was introduced in 1 mmol of carbonyl substrate and 1 ml of solvent. Methanol (anhydrous, 99.8%) or 1,3-propanediol (98%) was used. The reaction was stirred at room temperature or heated to reaction temperature, and monitored by GC-MS.

Example 1

In order to form the mesoporous poly-melamine-formaldehyde (mPMF), melamine and paraformaldehyde (1.8 eq) were reacted with 3.36 ml of anhydrous dimethyl sulfoxide (overall concentration of 2.5 M) at 170° C. for 72 hours. The resulting white polymer has a B.E.T. surface area of 930 m²/g, an average pore size of 15.7 nm, a total pore volume of 1.90 cm³/g, and a micropore volume of 0.21 cm³/g.

Example 2

Cinnamaldehyde was chosen as the model substrate as it contains an α,β-unsaturated C=C bond that is sensitive to acids and can result in double bond isomerization. mPMF was found to catalyse the formation of dimethyl acetal from cinnamaldehyde and methanol without isomerization. 2 mg of catalyst was used with 1 mmol of substrate and 1 ml of solvent, unless otherwise noted. The reaction reached equilibrium with 65% yield in 8 hours at room temperature (Entry 1, Table 1). Further, an increase in reaction time (Entry 1, Table 1) or reaction temperature (Entry 2, Table 1) did not result in an appreciable increase in yield, probably due to the presence of water as a by-product, which resulted in equilibrium between the reactant and the product.

In order to remove the water, trimethyl orthoformate (1.65 eq) was added as a drying agent. The resultant yield increased to 840 (Entry 3, Table 1).

Without the catalyst, no reaction was observed after 8 hours (Entry 4, Table 1).

mPMF was also treated with a base to remove the acidic groups on the polymer. When the base-treated mPMF was used as a catalyst, a decrease in yield was observed (Entry 5, Table 1). This confirmed the bifunctionality (that is, the acidic groups and the amine groups) of mPMF in catalysing the acetalization reaction.

When acetalization was conducted in 1,3-propanediol to form dioxane-protected cinnamaldehyde, a good yield of 830 could be obtained at room temperature for 24 hours (Entry 6, Table 1) or a yield of 85% could be achieved at 40° C. after 8 hours (Entry 7, Table 1) without the use of drying agents. As such, it is possible to reduce the reaction time from 24 hours to 8 hours by increasing the reaction temperature.

TABLE 1

Acetalization of trans-cinnamaldehyde over mPMF catalyst

| Entry | Catalyst | Additives | Temp (° C.) | Yield[a] (%) 8 hours | 24 hours |
|---|---|---|---|---|---|
| 1 | mPMF | — | RT[d] | 65 | 68 |
| 2 | mPMF | — | 40 | 64 | |
| 3 | mPMF | Trimethyl orthoformate | RT[d] | 84 | |
| 4 | — | — | RT[d] | 0 | 14 |
| 5 | mPMF[b] | — | RT[d] | 51 | |
| 6 | mPMF | 1,3-propanediol[c] | RT[d] | 65 | 83 |
| 7 | mPMF | 1,3-propanediol[c] | 40 | 85 | |

[a]GC yield.
[b]Base-treated mPMF.
[c]1,3-Propandiol was used instead of methanol.
[d]Room temperature or 25° C.

In order to determine the effects of increasing the amount of catalyst, acetalization reactions using 1 mmol of trans-cinnamaldehyde and 1 ml of 1,3-propanediol were carried out at room temperature (or 25° C.) using various amounts of catalyst (2 mg, 10 mg and 50 mg catalyst per mmol trans-cinnamaldehyde). The reaction times for each amount of catalyst were investigated for 4 hours, 8 hours and 24 hours. The results are shown in Table 2 below.

TABLE 2

Effect of Catalyst Loading

| Entry | Catalyst amount | Temperature (° C.) | Yield[a] (%) 4 hours | 8 hours | 24 hours |
|---|---|---|---|---|---|
| 1 | 2 mg | RT[b] | 46 | 62 | 83 |
| 2 | 10 mg | RT[b] | 66 | 77 | 89 |
| 3 | 50 mg | RT[b] | 61 | 81 | 94 |

[a]GC yield.
[b]room temperature or 25° C.

As shown in Table 2, by increasing the catalyst amount, the reaction time can be reduced from 24 hours to 8 hours.

In order to determine the effect of temperature at high catalyst loading, 1 mmol of trans-cinnamaldehyde was reacted with 1 ml of 1,3-propanediol in the presence of mg mPMF. The reactions were carried out at room temperature (25° C.), 40° C. and 60° C. for 2 hours, 4 hours and 8 hours. The results are shown in Table 3 below.

TABLE 3

Effect of Temperature at High Catalyst Loading

| Entry | Catalyst amount | Temperature (° C.) | Yield$^a$ (%) 2 hours | 4 hours | 8 hours |
|---|---|---|---|---|---|
| 1 | 50 mg | RT$^b$ | | 61 | 81 |
| 2 | 50 mg | 40 | 90 | 90 | 91 |
| 3 | 50 mg | 60 | 91 | 92 | 92 |

$^a$GC yield.
$^b$room temperature or 25° C.

As shown in Table 3, it is possible to further reduce reaction time to less than 2 hours by increasing the reaction temperature (from room temperature to 40° C.).

Example 3

The scope of substrates for acetalization with 1,3-propanediol was investigated over mPMF (Table 4). The reaction conditions were 1 mmol of substrate in 1 ml of 1,3-propanediol, 2 mg of mPMF for 24 hours, unless otherwise noted.

The reaction was found to be chemoselective to aldehydes, and did not react with ketones (Entries 2 and 3, Table 4). Ketones were less polar than aldehydes, and were thus not activated for acetalization over the mPMF catalyst. This mild protocol could thus be useful for the protection of aldehydes in the presence of ketones or acid-sensitive groups.

Excellent yields were obtained with benzaldehyde, achieving 94% yield (Entry 1, Table 4). In the presence of electron-donating groups on the benzene ring, such as methoxy group in the para-position (4-methoxybenzaldehyde) (Entry 4, Table 4), a good yield of 85% was obtained.

When solid substrates were used, the reaction temperature was increased from room temperature to 40° C. to improve their solubility in the reaction. At 40° C., 4-chlorobenzaldehyde gave a good yield of 760 (Entry 5, Table 4) while the yield decreased to 48% when 4-bromobenzaldehyde was used (Entry 6, Table 4).

For substrates with electron-withdrawing groups in the para-position, no reaction was observed (Entries 7 and 8, Table 4) due to the lower electrophilicity of the aldehyde carbon.

Other functional groups in the para-position such as methyl ester and phenyl ring gave yields of 90% and 54%, respectively, at 60° C. (Entries 9 and 10 respectively, Table 4).

Ortho-substituted electron-donating substrates, such as salicylaldehyde gave a good yield of 84% within 8 hours (Entry 11, Table 4).

Reaction with 4-nitrocinnamaldehyde proceeded well with 87% yield (Entry 12, Table 4).

However, in the presence of methyl group at the α-position of cinnamaldehyde, the yield decreased to 52%, likely due to steric hindrance (Entry 13, Table 4).

The reaction also proceeded well with aldehyde substrates, such as 2-naphthaldehyde, obtaining 75% yield (Entry 14, Table 4).

TABLE 4

Acetalization of various substrates

| Entry | Substrate | Temperature (° C.) | Yield$^a$ (%) |
|---|---|---|---|
| 1 | Benzaldehyde | RT$^f$ | 94 |
| 2 | Acetophenone | 40 | —$^b$ |

TABLE 4-continued

Acetalization of various substrates

| Entry | Substrate | | Temperature (° C.) | Yield[a] (%) |
|---|---|---|---|---|
| 3 | 4-Phenyl-2-butanone | | 40 | —[b] |
| 4 | 4-Methoxybenzaldehyde | | RT[f] | 85 |
| 5 | 4-Chlorobenzaldehyde | | 40 | 76 |
| 6 | 4-Bromobenzaldehyde | | 40 | 48 |
| 7 | 4-Nitrobenzaldehyde | | 40 | — |
| 8 | 4-Cyanobenzaldehyde | | 40 | — |
| 9 | Methyl-4-formylbenzoate | | 60 | 90[c,d] |
| 10 | Biphenyl-4-carboxaldehyde | | 60 | 54[d] |

TABLE 4-continued

Acetalization of various substrates

R-CHO + HO-CH₂CH₂CH₂-OH →(mPMF catalyst, neat)→ 1,3-dioxane product

| Entry | Substrate | Temperature (°C) | Yield[a] (%) |
|---|---|---|---|
| 11 | Salicylaldehyde | 40 | 84[d,e] |
| 12 | Trans-4-nitrocinnamaldehyde | 40 | 87 |
| 13 | α-Methyl-trans-cinnamaldehyde | RT[f] | 52 |
| 14 | 2-Naphthaldehyde | 60 | 75[d] |

[a]GC yield.
[b]No reaction.
[c]Reaction time: 32 hours.
[d]0.5 ml of 1,3-propanediol was used.
[e]Reaction time: 8 hours
[f]Room temperature or 25° C.

Example 4

Figure 2:
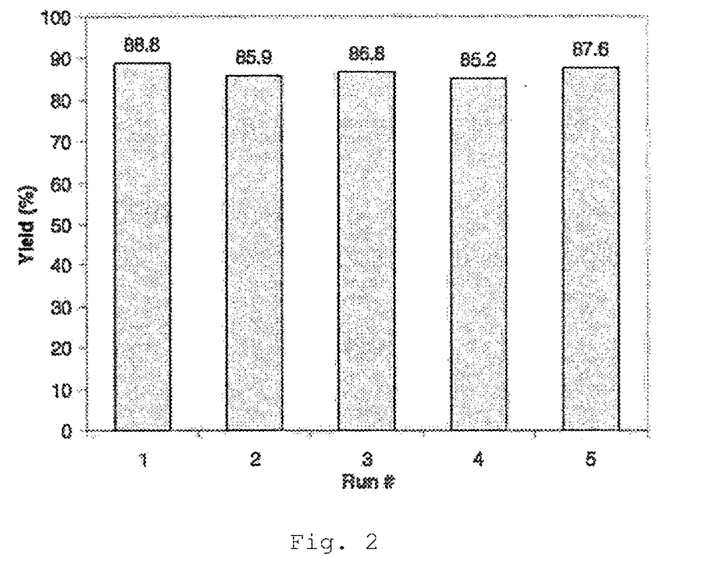
FIG. 2 is a graph showing the yield obtained from five acetalization reactions with the same catalyst.

The ability of mPMF to be reused and recycled was investigated. Here, 2.5 mmol of trans-cinnamaldehyde in 2.5 mol of 1,3-propanediol was reacted in the presence of 5 mg mPMF at room temperature (or 25° C.) for 48 hours. After each reaction, the reaction mixture was filtered. The filtrate was collected, extracted with $CH_2Cl_2$, washed with $H_2O$ and brine and dried over $Na_2SO_4$. The organic layer was concentrated in vacuo, and the NMR spectrum was collected. The solid catalyst was washed with methanol and $CH_2Cl_2$, and dried for further recycling studies. As shown in FIG. 2, the mPMF was used for a further four times without any substantial loss in its catalytic activity since the yield obtained did not differ appreciably between the different runs using the same catalyst.

Comparative Example

Since the amine groups in mPMF were found to catalyse acetalization reaction, similar small molecule amines such as melamine, 3-aminopyridine and 4-aminopyridine were investigated for their catalytic effect (Table 5).

Here, 1 mmol of trans-cinnamaldehyde in 1 ml of anhydrous methanol were reacted in the presence of 10 mold test amine at 60° C. for 32 hours.

Reaction using melamine resulted in a product with 31% yield (Entry 1, Table 5).

Reaction using 2-aminopyridine resulted in the decomposition of the reaction mixture, yielding a dark brown mixture (Entry 2, Table 5).

It was observed that with 3-aminopyridine, which has an amine group in close proximity to the nitrogen on the pyridine ring, moderate product yield of 53% was obtained after 32 hours (Entry 3, Table 5).

With 4-aminopyridine, almost no reaction occurred after 32 hours (Entry 4, Table 5). This could be due to the high pKa of 4-aminopyridine or the weaker hydrogen bonding activation of the aldehyde substrate with the para-position of the aminopyridine.

With 2-aminopyrimidine, 47% yield was obtained (Entry 5, Table 5).

The use of 2-pyridinol led to the corresponding acetal at a moderate yield of 52%, despite its high pKa value of 11.7 (Entry 6, Table 5). This indicated that hydrogen activation played a major role in acetal formation.

As shown, the reactions using small amine molecules were slow and sluggish. In comparison, the mPMF catalyst resulted in improved yield in shorter reaction times.

TABLE 5

Acetalization of trans-cinnamaldehyde over amine

| Entry | Amine | pK$_a$ | Yield$^a$ (%) |
|---|---|---|---|
| 1 | Melamine | 5.0 | 31 |
| 2 | 2-Aminopyridine | 6.9 | —$^b$ |
| 3 | 3-Aminopyridine | 6.0 | 53 |
| 4 | 4-Aminopyridine | 9.2 | 2 |
| 5 | 2-Aminopyrimidine | 3.5 | 47 |
| 6 | 2-Pyridinol | 11.7 | 52 |

$^a$GC yield.
$^b$Decomposition of reaction was observed.

APPLICATIONS

The disclosed method may be used to acetalize aldehydes with high yields under mild reaction conditions. The method may be compatible with acid-sensitive substrates. The method may not require the use of high reaction temperatures. The method may not require the use of co-solvent. The method may not require the use of metal-based catalyst.

The catalyst may be recycled and reused without any substantial loss in its catalytic activity. The catalyst may be formed easily from common industrial chemicals (such as melamine and paraformaldehyde) in a one-step reaction. The catalyst may be easy to synthesize and can be obtained at a low cost.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method of acetalizing an aldehyde comprising reacting said aldehyde with an alcohol in the presence of a polymeric catalyst to form an acetal,
wherein the polymeric catalyst comprises monomers that are capable of participating in double hydrogen bonding with said aldehyde and is a mesoporous poly-melamine-formaldehyde.

2. The method of claim 1, wherein said polymeric catalyst has a pH in the acidic range.

3. The method of claim 2, wherein said polymeric catalyst has a pH in the range of 4 to 6.

4. The method of claim 1, wherein said mesopores are disposed between melamine-formaldehyde co-polymer nanoparticles and wherein micropores extend within said co-polymer nanoparticles.

5. The method of claim 4, wherein said melamine-formaldehyde co-polymers are composed of repeating units of monomers which have a ring structure.

6. The method of claim 5, wherein said ring structure is of the following Formula I:

Formula I

7. The method of claim 1, wherein said reacting occurs at a temperature selected from the range of 25° C. to 60° C.

8. The method of claim 1, wherein the ratio of alcohol to aldehyde is in the range of 5:1 to 50:1.

9. The method of claim 1, wherein the amount of said porous polymeric catalyst is in the range of 2 mg to 50 mg per 1 mmol of said aldehyde.

10. The method of claim 1, further comprising adding a drying agent.

11. The method of claim 1, further comprising the step of separating the catalyst from said acetal.

12. The method of claim 11, further comprising the step of reusing said separated catalyst in a subsequent acetalization reaction.

* * * * *